United States Patent [19]

Stern

[11] 4,404,207
[45] Sep. 13, 1983

[54] ANTIMICROBIAL 8-SUBSTITUTED BENZO[IJ]QUINOLIZINES

[75] Inventor: Richard M. Stern, Cottage Grove, Minn.

[73] Assignee: Riker Laboratories, Inc., St. Paul, Minn.

[21] Appl. No.: 318,929

[22] Filed: Nov. 6, 1981

[51] Int. Cl.$^3$ ............... A01N 43/42; A61K 31/47; C07D 455/04
[52] U.S. Cl. .................................. 424/258; 546/94
[58] Field of Search .......................... 546/94; 424/258

[56] References Cited

U.S. PATENT DOCUMENTS

| | | | |
|---|---|---|---|
| 3,896,131 | 7/1975 | Gerster | 546/94 |
| 3,985,882 | 10/1976 | Gerster | 424/258 |
| 4,238,487 | 12/1980 | Bicking | 546/196 X |
| 4,251,537 | 2/1981 | Evans | 546/196 X |
| 4,281,014 | 7/1981 | Yaffee | 546/196 X |

FOREIGN PATENT DOCUMENTS

| | | | |
|---|---|---|---|
| 55-27204 | 9/1980 | Japan | 546/94 |
| 55-131632 | 9/1980 | Japan | 546/94 |
| 55-59121 | 11/1980 | Japan | 546/94 |
| 55-61776 | 11/1980 | Japan | 546/94 |
| 56-131630 | 2/1981 | Japan | 546/94 |
| 56-106776 | 12/1980 | Japan | 546/94 |
| 56-131629 | 5/1981 | Japan | 546/94 |
| 56-131631 | 5/1981 | Japan | 546/94 |
| 56-135807 | 5/1981 | Japan | 546/94 |

*Primary Examiner*—Richard A. Schwartz
*Attorney, Agent, or Firm*—Cruzan Alexander; Donald M. Sell; Carolyn A. Bates

[57] ABSTRACT

Antimicrobial compounds of the following formula are disclosed:

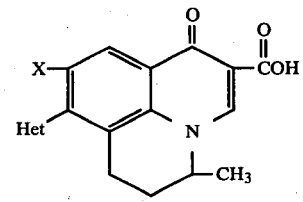

wherein Het is selected from the goup consisting of pyrryl, pyrrolidyl, tetrazolyl of the formula

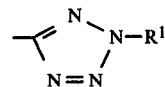

wherein $R^1$ is lower alkyl or benzyl and oxadiazolyl of the formula

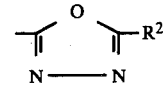

wherein $R^2$ is lower alkyl, trifluoromethyl or —NHφ—; X is hydrogen and when Het is pyrryl or pyrrolidyl, X may be fluorine. Pharmaceutically acceptable carboxylate salts and esters of the acids are also disclosed.

11 Claims, No Drawings

ANTIMICROBIAL 8-SUBSTITUTED BENZO [IJ]QUINOLIZINES

TECHNICAL FIELD

This invention relates to derivatives of the heterocyclic system known as benzo[ij]quinolizine. More specifically, it relates to 6,7-dihydro-5-methyl-1-oxo-1H,5H-benzo[ij]quinolizine-2-carboxylic acids substituted at the 8-position and pharmaceutically-acceptable carboxylate salts and esters thereof. The use of these compounds as antimicrobial agents and pharmaceutical compositions containing these compounds are also included within the scope of the invention.

BACKGROUND ART

U.S. Pat. Nos. 3,896,131 and 3,985,882 described benzo[ij]quinolizine-2-carboxylic acids which are useful antimicrobial agents. The prior art compounds may contain various substituents in the 8, 9 or 10-position including amino ($-NH_2$), N,N-dimethylamino [$(CH_3)_2N-$], alkanamido and trifluoroacetamido groups. However, prior to the present invention, it was not known that compounds substituted in the 8-position with five-membered-nitrogen-containing heterocyclic nuclei exhibit useful antimicrobial activity.

DESCRIPTION OF THE INVENTION

The invention relates to derivatives of benzo[ij]-quinolizine-2-carboxylic acid of the formula

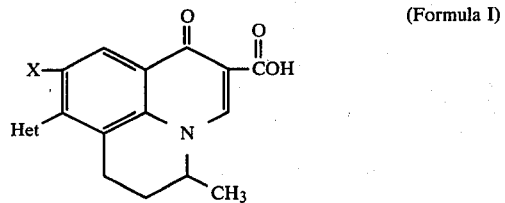

(Formula I)

wherein Het is selected from pyrryl, pyrrolidyl, tetrazolyl of the formula

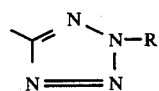

wherein R is lower alkyl or benzyl, and oxadiazolyl of the formula

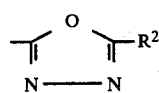

wherein $R^2$ is lower alkyl, trifluoromethyl or $-NH\phi$; X is hydrogen; and when Het is pyrryl or pyrrolidyl, X may also be fluoro; and pharmaceutically-acceptable carboxylate salts, esters and alkylaminoalkyl ester salts thereof.

The term "lower" as used herein to describe "alkyl" means an alkyl group having 1 to 4 carbon atoms in straight or branched chain configuration.

Compounds of the invention have an optically active carbon at the 5-position. All such optical isomers are included within the scope of the invention.

It is well known in the art that pharmaceutically acceptable salts such as alkali metal, alkaline earth, aluminum, iron and other metal and amine salts of pharmaceutically active acids are the equivalents of the acids, and in some cases may even offer advantages in absorption, formulation and the like. Salts of the free acid compounds of the invention are readily prepared by reaction of the acid with a base and evaporation to dryness. The base may be organic, e.g., sodium methoxide or an amine, or inorganic, e.g., sodium hydroxide.

Esters of the acids of Formula I may be obtained as intermediates during the preparation of the acids, or, in some cases, the esters may be prepared directly using standard synthetic methods. The esters exhibit antimicrobial activity but are primarily of interest as synthetic intermediates, although in some instances hydrolyzable or salt-forming esters may be of interest as therapeutic agents. Preferred esters of the invention are alkyl esters and alkylaminoalkyl esters having one to four carbon atoms in the alkyl group. Especially preferred are aminoalkyl esters which will form salts, e.g., hydrochlorides, such as the dimethylaminoethyl esters.

The esters are readily prepared by reacting the free acid of Formula I with thionyl chloride to provide the novel acyl chloride derivative. The acyl chloride is reacted with the appropriate alcohol to provide the desired ester.

The antimicrobial activity of the compounds of the present invention can be demonstrated by the known, standard plate dilution method for bacterial susceptibility to antibiotics. The culture medium employed permits susceptibility testing of fastidious microorganisms towards antibiotics, sulfonamides and other chemotherapeutic agents. Tryptone soy agar (oxoid) of the following composition is the culture medium.

| | |
|---|---|
| Oxoid tryptone | 15 g. |
| Oxoid soy peptone | 5 g. |
| Sodium chloride | 5 g. |
| Oxoid agar-agar No. 3 | 15 g. |
| Water | 1 liter |

Using this test, the compounds of the invention have been found to have a broad spectrum of activity against gram-positive and gram-negative microorganisms.

The compounds of the invention are active against microorganisms either in the absence or presence of 10 percent horse serum.

The test procedure used to determine activity as employed in connection with the present invention provides information on the amount of a compound required to give complete inhibition, partial inhibition or no inhibition of microbial growth on the agar plates. In the tests, the test compound is added to the agar medium to give concentrations of zero, one, ten and one hundred milligrams per liter. A series of plates with these concentrations is prepared. Ten percent horse serum is added to one series of such plates. Aliquots of broth culture of each of twelve species of microorganisms are innoculated onto the agar plates containing the various test compound concentrations. The plates are incubated at 37° C. in a 10 percent carbon dioxide atmosphere for 18–24 hours. The microbial growth on each plate is read visually, and minimal inhibitory concentrations are recorded. Some of the microorganisms which are used for this test are:

1. *Staphylococcus aureis*
2. *Bacillus subtilis*

3. *Escherichia coli*
4. *Pseudomonas aeruginosa*
5. *Streptococcus sp.**
6. *Asperigillus niger*
7. *Candida albicans*
8. *Acinetobacter lwoffi*
9. *Acinetobacter anitratum*
10. *Klebsiella pneumoniae*
11. *Streptococcus fecaelis*
12. *Serratia marcescens*

*strains isolated from dental caries in rats or hamsters at the National Institute of Dental Health and grown in PFY or APT agar.

All of the compounds of the invention possess antimicrobial activity towards one or more of the above microorganisms.

Some of the compounds of the invention have also shown activity against one or more anaerobic bacteria, for example, Bacteroides sp. and *Clostridium welchii*. Some compounds of the invention have shown useful activity towards *Erwinia amylovora*, a gram-negative microorganism responsible for the plant disease known as fire blight.

It will be understood by those skilled in the art that the species used are representative indicator species, as it would be impractical to screen against all microorganisms. It is well known in the art that broad spectrum activity can be predicted on the basis of activity shown against selected representative species of microorganisms.

Some of the compounds of the invention are active when administered orally to animals. They are excreted in the urine, and are effective urinary tract antibacterials in mammals. It is also contemplated that they may be used in the treatment of pulmonary infections, soft tissue infections, burn infections and bacteremias.

All of the compounds of the invention are active against microorganisms in vitro or topically. In vitro activity is useful in itself, since antimicrobial agents may be used for disinfecting and sterilizing, e.g., medical and dental equipment, as components of disinfecting solutions. The compounds of the invention are also active in vivo in animals.

The acute oral toxicity of the compounds of the invention is generally moderate to low compared with the effective oral dose, and they have an acceptable therapeutic ratio ($LD_{50}/ED_{50}$).

The carboxylic acid compounds of the invention are ordinarily white or yellowish crystalline or amorphous materials when purified. They are substantially insoluble in water, lower alcohols or hydrocarbons and are more soluble in halogenated solvents, N,N-dimethylformamide and the like. The esters are generally somewhat more soluble in organic solvents. The salts, especially the alkali metal salts, have appreciable solubility in water and lower alcohols.

The compounds of the invention may be formulated by incorporating them into conventional pharmaceutical vehicles, either organic or inorganic, which are suitable for oral or intraperitoneal application. For in vitro or topical use, simple aqueous solutions or suspensions are most conveniently employed. For this purpose, concentrations of the order of 100 parts per million up to about 5 parts per thousand are suitable, and the formulation is used by immersing objects to be treated therein, or by local application to an infected area.

The amount of compound to be used to treat, e.g., a microbial urinary infection by oral administration will be an effective amount less than a toxic amount. The amount to be administered to control an infection will depend on the species, sex, weight, physical condition and many other factors, but this judgment is well within the skill of the medical art. Usually the amount will be less than 100 mg/kg per dose. Conveniently this is administered in the form of conventional pharmaceutical preparations such as capsules, tablets, emulsions, solutions and the like. Excipients, fillers, coatings, etc. are generally employed with tablets or capsules, as is well known in the art.

It is known to the art that antimicrobial agents are used as growth promoters in various animal and bird species. Although not yet verified, it is inferred from the outstanding antimicrobial activity that the compounds of the invention can be used for this purpose also. The compounds of the invention may also be used for the control of microbial (e.g., *Erwinia amylovora*) infections of plants, e.g., by spraying or dusting formulation of these compounds on the affected area.

The compounds of the invention are prepared starting with known compounds. The 9-fluoro-substituted compounds start with the known 6-fluoroquinaldine which is nitrated with fuming nitric and sulfuric acids in the presence of sodium nitrite catalyst to provide the compound 6-fluoro-5-nitro-quinaldine.

The nitro group is reduced catalytically, for example, in the presence of palladium on charcoal. If this reaction is carried out in the presence of acetic anhydride, the product is the compound 5-acetamido-6-fluoroquinaldine. This intermediate is further reduced catalytically in the presence of platinum on charcoal to provide the compound 5-acetamido-6-fluorotetrahydroquinaldine.

The tetrahydroquinaldine intermediate is condensed with diethyl ethoxymethylenemalonate by heating without solvent at 100°–200° C. (preferably 140°–150° C. for two hours) for several hours. The intermediate is the compound of the formula (II)

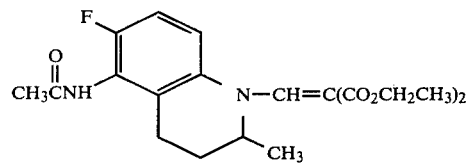

II

This intermediate is an oil which need not be isolated or purified. Instead, polyphosphoric acid is added, and the solution is heated at 100°–140° C. to effect a condensation to provide an ester of the acids of Formula I wherein Het is acetamido. The next step is saponification of the esters and hydrolysis of the acetamido group to provide 8-amino-6,7-dihydro-9-fluoro-5-methyl-1-oxo-1H,5H-benzo[ij]quinolizine-2-carboxylic acid, a key intermediate.

Compounds of the invention wherein X is hydrogen are prepared from 5-aminoquinaldine by blocking the amino group as acetamido and converting to 8-acetamido-6,7-dihydro-5-methyl-1-oxo-1H,5H-benzo[ij]quinolizine-2-carboxylic acid, then hydrolyzing to the 8-amino compound.

The 8-amino intermediate (wherein X is hydrogen) is converted to the 8-cyano derivative by the sequence of diazotization in the presence of fluoroboric acid, isolation of the fluoroborate salt and heating the salt in the presence of a cyanide salt, preferably cuprous cyanide, in a very polar solvent such as dimethyl sulfoxide.

In order to prepare the intermediate 8-cyano-6,7-dihydro-9-fluoro-5-methyl-1-oxo-1H,5H-benzo[ij]-quinolizine-2-carboxylic acid one starts with 2-fluorobenzoic acid and nitrates. Nitration with concentrated nitric and concentrated sulfuric acids at moderate temperatures (15°–25° C.) provides 2-fluoro-5-nitrobenzoic acid. Catalytic reduction, e.g., with palladium on charcoal catalyst, provides 5-amino-2-fluorobenzoic acid. Condensation of this aromatic amine with crotonaldehyde in the presence of ferrous sulfate heptahydrate and sodium m-nitrobenzenesulfonate provides 5-carboxyl-6-fluoroquinaldine. The carboxyl group is reacted with thionyl chloride to provide the carboxyl chloride which is reacted with ammonium hydroxide to provide 5-carboxamido-6-fluoroquinaldine. Dehydration of the carboxamido group in pyridine with trifluoroacetic anhydride in an inert solvent such as dichloromethane provides 5-cyano-6-fluoroquinaldine. This intermediate condenses with diethyl ethoxymethylenemalonate to yield an intermediate of Formula II where the 5-position is substituted by cyano. Condensation in polyphosphoric acid provides the benzo[ij]quinolizine ring, but the cyano group may be partially hydrolyzed and again require dehydration with pyridine and trifluoroacetic anhydride. Hydrolysis of the carboxylic ester group in the 2-position may also be required to obtain the desired intermediate.

The 8-cyano intermediate wherein X is hydrogen may also be prepared using the latter route starting with the known compound 5-carboxylquinaldine. It has been found that this is the preferred synthetic route for both the 9-fluoro and the 9-hydro compounds.

The 8-pyrryl compounds of the invention are prepared by reacting the corresponding 8-amino compounds by heating with 2,5-dimethoxytetrahydrofuran in an organic acid such as acetic acid.

The 8-pyrrolidyl compounds of the invention are prepared by catalytic reduction of the corresponding 8-pyrryl compounds. Suitable catalysts include palladium on charcoal and rhodium on alumina.

The 8-tetrazolyl compounds of the invention are prepared by reacting the corresponding 8-cyano intermediate with hydrazoic acid generated by action of ammonium chloride on sodium azide. This reaction is carried out in a strongly polar solvent such as N,N-dimethylformamide.

The 8-tetrazolyl compound of the invention is used as an intermediate to prepare compounds wherein the 2-position of the tetrazole ring is substituted by alkyl of one to four carbon atoms or benzyl. This reaction is carried out by reacting the proton of the tetrazole ring with a strong base such as sodium hydride, and then reacting an alkyl or benzyl halide with the activated nitrogen of the tetrazole ring.

The 8-tetrazolyl compounds of the invention are also used to prepare the 8-oxadiazolyl compounds of the invention by reaction with organic anhydrides such as trifluoroacetic anhydride, acetic anhydride or other anhydrides. The resulting 8-oxadiazolyl compounds are substituted at the 2-position of the oxadiazolyl moiety.

The 8-tetrazolyl compounds of the invention are also reacted with organic isocyanates to provide 8-oxadiazolyl compounds substituted at the 2-position of the oxadiazolyl moiety by an arylamino or alkylamino group.

The invention may be further illustrated by reference to the following non-limiting examples.

Preferred compounds of the invention due to their potency and broad spectrum of activity are the compounds of Examples 2, 3, 9, 10, 12, 13, 14 and 15.

EXAMPLE 1

Part A. 6-Fluoro-5-nitroquinaldine

To 3.5 l of fuming sulfuric acid was added, with cooling, 600 g (3.73 moles) of 6-fluoroquinaldine in small portions. To this mixture was added about 0.1 g of sodium nitrite, followed by the dropwise addition of 261 ml of fuming red nitric acid over a six hour period while maintaining the temperature at 5°–10° C. The mixture was stirred at 20° C. for sixteen hours and poured into 3 gallons of ice. The mixture was basified with ammonium hydroxide, with cooling. The precipitated solid was separated by filtration, then dissolved in about two liters of warm toluene. The solution as dried over magnesium sulfate, filtered and evaporated to provide the yellow solid 6-fluoro-5-nitroquinaldine, m.p. 105°–108° C., which was recrystallized from 1,2-dichloroethane. The structural assignment was confirmed by nuclear magnetic resonance and infrared spectral analyses.

Part B. 5-Acetamido-6-fluoroquinaldine

To a mixture of 20 g (0.1 mole) of 6-fluoro-5-nitroquinaldine in 180 ml of ethyl acetate and 20 ml of acetic anhydride was added 3 g of ten percent palladium on charcoal. The mixture was hydrogenated with hydrogen gas at 50 psi on a Parr apparatus for 20 minutes. The theoretical amount of hydrogen (25 psi) was used. On cooling the mixture solidified to a yellow mass. About 200 ml of ethanol was added, and the mixture was heated to dissolve the product. The catalyst was removed by filtration through celite and the filtrate was evaporated to dryness, leaving a yellow solid. The solid was triturated with 200 ml of water and neutralized with ten percent sodium hydroxide solution. Filtration and drying provided white crystals of 5-acetamido-6-fluoroquinaldine, m.p. 232°–235° C. The structural assignment was confirmed by infrared spectral analysis.

Part C. 5-Acetamido-6-fluorotetrahydroquinaldine

In one liter of acetic acid was dissolved 95 g of 5-acetamido-6-fluoroquinaldine. To this mixture was added 10 g of five percent platinum on charcoal. The mixture was hydrogenated with hydrogen gas at 30 psi on a Parr apparatus for five hours. The amount of hydrogen used was 61 psi (versus 62 psi theoretical). The catalyst was removed by filtration, the filtrate was concentrated to 250 ml and decanted into cold stirred sodium hydroxide solution. The white precipitate was separated by filtration and triturated with a chloroform/hexane (50/50) mixture to provide white crystals of 5-acetamido-6-fluorotetrahydroquinaldine, m.p. 168°–170° C. The structural assignment was confirmed by infrared spectral analysis.

Part D. Diethyl 2-[N-(5-Acetamido-6-fluorotetrahydroquinaldinyl)]methylenemalonate A stirred mixture of 6.4 g (28.8 mmole) of 5-acetamido-6-fluorotetrahydroquinaldine and 8 g (37 mmole) of diethyl ethoxymethylenemalonate was heated at 140°–150° C. for two hours. Ethanol was allowed to evolve. The product, diethyl 2-[N-(5-acetamido-6-fluorotetrahydroquinaldinyl)]methylenemalonate was not isolated.

Part E.
8-Amino-6,7-dihydro-9-fluoro-5-methyl-1-oxo-1H,5H-benzo[ij]quinolizine-2-carboxylic Acid The reaction mixture of part D, containing diethyl 2-[N-(5-acetamido-6-fluorotetrahydroquinaldinyl]methylenemalonate was treated with 25 g of polyphosphoric acid and warmed to 100° C. for 5 minutes while stirring. Foaming was observed, demonstrating that reaction had commenced. The external heating was removed and stirring was continued for ten minutes. Heat was reapplied and the mixture was maintained at 100° C. for 0.5 hour. The cyclized product was then hydrolyzed (ester portion) and deacetylated (acetamido group) by adding 150 ml of water and 25 ml of methanol, basifying cautiously with fifty percent sodium hydroxide solution and heating at reflux for 2.5 hours.

Filtration through decolorizing charcoal and celite and decantation into rapidly stirring dilute acetic acid provided a tan solid, hydrated 8-amino-6,7-dihydro-9-fluoro-5-methyl-1-oxo-1H,5H-benzo[ij]quinolizine-2-carboxylic acid, m.p. 300° C. Analysis: Calculated for $C_{14}H_{13}FN_2O.\frac{1}{2}H_2O$; %C, 59.5; %H, 4.8; %N, 9.9; Found: %C, 59.1; %H, 4.5; %N, 9.8.

EXAMPLE 2

To a suspension of 1.0 g of 8-amino-6,7-dihydro-9-fluoro-5-methyl-1-oxo-1H,5H-benzo[ij]quinolizine-2-carboxylic acid in 20 ml of warm galcial acetic acid was added 1.0 g 2,5-dimethoxytetrahydrofuran. The mixture was heated at reflux for 30 minutes. The product which precipitated was separated by filtration and washed with water to provide yellowish-white crystals of 6,7-dihydro-9-fluoro-5-methyl-1-oxo-8-(1-pyrryl)-1H,5H-benzo[ij]quinolizine-2-carboxylic acid hydrate, m.p. 300° C. Analysis: Calculated for $C_{18}H_{15}FN_2O_3.\frac{1}{2}H_2O$: %C, 65.0; %H, 4.7; %N, 8.4; Found: %C, 64.8; %H, 4.5; %N, 8.4. The structural assignment was confirmed by infrared and nuclear magnetic resonance spectral analyses.

EXAMPLE 3

To a solution of 3.6 g of 6,7-dihydro-9-fluoro-5-methyl-1-oxo-8-(1-pyrryl)-1H,5H-benzo[ij]quinolizine-2-carboxylic acid in 50 ml of trifluoroacetic acid was added 2.0 g ten percent palladium on charcoal. The mixture was hydrogenated on a Paar apparatus for two hours at 50 psi at 50° C. The mixture was filtered, and the filtrate was evaporated. The residue was mixed with 50 ml of water and the pH adjusted to 5 by the addition of ten percent sodium hydroxide solution and acetic acid. The precipitate obtained was recrystallized from aqueous N,N-dimethylformamide (80%) to provide tan crystals of 6,7-dihydro-9-fluoro-5-methyl-1-oxo-8-(1-pyrrolidyl)-1H,5H-benzo[ij]quinolizine-2-carboxylic acid, m.p. 243°–245° C. Analysis: Calculated for $C_{18}H_{19}FN_2O_3$: %C, 65.5; %H, 5.8; %N, 8.5; Found: %C, 65.8; %H, 5.8; %N, 8.5. The structural assignment was confirmed by infrared and nuclear magnetic resonance spectral analyses.

EXAMPLE 4

Using the method of Example 1 and starting with the known compound 5-acetamidoquinaldine, 8-amino-6,7-dihydro-5-methyl-1-oxo-1H,5H-benzo[ij]quinolizine-2-carboxylic acid hydrate, m.p. 238°–240° C., was obtained. Analysis: Calculated for $C_{14}H_{14}N_2O_3.H_2O$: %C, 60.9; %H, 5.8; %N, 10.1; Found: %C, 61.2; %H, 5.9; %N, 10.3.

EXAMPLE 5

To a suspension of 3.0 g of 8-amino-6,7-dihydro-5-methyl-1-oxo-1H,5H-benzo[ij]quinolizine-2-carboxylic acid in 30 ml of glacial acetic acid was added 3.0 g of 2,5-dimethoxytetrahydrofuran and the mixture was heated on a steam bath for 1.5 hours. Cooling produced a solid which was separated by filtration to provide 6,7-dihydro-5-methyl-1-oxo-8-(1-pyrryl)-1H,5H-benzo[ij]quinolizine-2-carboxylic acid, m.p. 303°–305° C. Analysis: Calculated for $C_{18}H_{16}N_2O_3$: %C, 70.1; %H, 5.2; %N, 9.1; Found: %C, 69.5; %H, 5.1; %N, 9.2. The structural assignment was confirmed by infrared spectral analysis.

EXAMPLE 6

Using the method of Example 5, 3.0 g of 8-amino-6,7-dihydro-5-methyl-1-oxo-1H,5H-benzo[ij]quinolizine-2-carboxylic acid was converted to 6,7-dihydro-5-methyl-1-oxo-8-(1-pyrryl)-1H,5H-benzo[ij]quinolizine-2-carboxylic acid. The crude product was dissolved in 50 ml of trifluoroacetic acid and 2 g of rhodium on alumina was added. The mixture was hydrogenated at 20° C. for 18 hours at 50 psi of hydrogen gas. The mixture was filtered, evaporated to dryness and dissolved in 10 percent sodium hydroxide solution. The solution was acidified with glacial acetic acid. The product was recrystallized from N,N-dimethyformamide to provide tan crystals of 6,7-dihydro-5-methyl-1-oxo-8-(1-pyrrolidyl)-1H,5H-benzo[ij]quinolizine-2-carboxylicacid, m.p. 170°–174° C. Nuclear magnetic resonance analysis showed water and N,N-dimethyl formamide present in the solid. Analysis: Calculated for $C_{18}H_{20}N_2O_3.1/10(CH_3)_2NCHO.\frac{1}{2}H_2O$: %C, 66.8; %H, 6.6; %N, 9.2; Found: %C, 66.7; %H, 6.2; %N, 9.2.

EXAMPLE 7

Step A

To 250 ml of hot 48% fluoroboric acid was added 50 g of 8-amino-6,7-dihydro-5-methyl-1-oxo-1H,5H-benzo[ij]quinolizine-2-carboxylic acid. The solution was gradually cooled to 0° C. and 16.8 g of sodium nitrite in 50 ml of water was added slowly with vigorous stirring. After stirring about 30 minutes at 0° C., 250 ml of an ice water mixture was added. Stirring was continued for about thirty minutes. The solid was separated by filtration and washed sequentially with an isopropanol-fluoroboric acid mixture, isopropanol, an isopropanol-diethyl ether mixture, and diethyl ether. The product, 8-diazonium-6,7-dihydro-5-methyl-1-oxo-1H,5H-benzo[ij]quinolizine-2-carboxylic acid fluoroborate, was a gold solid.

Step B

A mixture of 81 g of cuprous cyanide and 57 g of sodium cyanide in 550 ml of dimethyl sulfoxide was heated on a steam bath until the solids were dissolved. After cooling to 25° C., 55 g of 8-diazonium-6,7-dihydro-5-methyl-1-oxo-1H,5H-benzo[ij]quinolizine-2-carboxylic acid fluoroborate in 275 ml of dimethyl sulfoxide was added slowly with rapid stirring. The temperature was maintained below 30° C. for one hour after the completion of the addition. The mixture was then poured into 5 liters of water. The tan solid was separated by filtration and recrystallized from N,N-dimethylformamide to provide 8-cyano-6,7-dihydro-5-methyl-1-oxo-1H,5H-benzo[ij]quinolizine-2-carboxylic acid, m.p. >300° C. Analysis: Calculated for $C_{15}H_{12}N_2O_3$: %C, 67.2; %H, 4.5; %N, 10.4; Found: %C, 67.1; %H, 4.8; %N, 10.1.

EXAMPLE 8

A mixture of 1.4 g (5 mmole) of 8-cyano-6,7-dihydro-5-methyl-1-oxo-1H,5H-benzo[ij]quinolizine-2-carboxylic acid, 0.75 g (11 mmole) of sodium azide, 0.6 g (11 mmole) of ammonium chloride and 50 ml of N,N-dimethylformamide was heated at 120° C. for three days in a sealed vessel followed by decantation into 100 ml of water. To this mixture was added 2 ml of glacial acetic acid, and the mixture was cooled. The solid was separated by filtration and recrystallized from aqueous N,N-dimethylformamide to provide white needles of 6,7-dihydro-5-methyl-1-oxo-8-(5-tetrazolyl)-1H,5H-benzo[ij]quinolizine-2-carboxylic acid, m.p. 270° C. (dec.). Analysis: Calculated for $C_{15}H_{13}N_5O_3$: %C, 57.9; %H, 4.2; %N, 22.5; Found: %C 57.8; %H, 4.0; %N, 22.7. The structural assignment was confirmed by infrared and nuclear magnetic resonance spectral analyses.

EXAMPLE 9

A solution of 3.5 g (11.2 mmole) of 6,7-dihydro-5-methyl-1-oxo-8-(5-tetrazolyl)-1H,5H-benzo[ij]quinolizine-2-carboxylic acid in 100 ml of N,N-dimethylformamide was heated to reflux, then allowed to cool. Sodium hydride (1.2 g of a 50% oil dispersion, 22 mmoles) was added and the mixture was heated at 60° C. for 20 minutes. To this mixture was added 5 ml (80 mmoles) of methyl iodide. The solution was stirred for four hours at 20° C. The mixture was warmed to 100° C. for 5 minutes, then 300 ml of water was added. After cooling the solid was collected by filtration and treated with 105 ml of 1.0% sodium hydroxide solution and 25 ml of methanol. This mixture was heated on a steam bath for 30 minutes. The mixture was filtered, concentrated to 75 ml and cooled. The product obtained was white crystals of sodium 6,7-dihydro-5-methyl-8-(2-methyl-5-tetrazolyl)-1-oxo-1H,5H-benzo[ij]quinolizine-2-carboxylate hydrate, m.p. 242° C. (dec). Analysis: Calculated for $C_{16}H_{14}N_5NaO_3 \cdot 1.5H_2O$: %C, 51.3; %H, 4.6; %N, 18.7; Found: %C, 51.2; %H, 4.7; %N, 18.9.

EXAMPLE 10

To a solution of 1.7 g (5.4 mmole) of 6,7-dihydro-5-methyl-1-oxo-8-(5-tetrazolyl)-1H,5H-benzo[ij]quinolizine-2-carboxylic acid in 50 ml of N,N-dimethylformamide was added 0.6 g of sodium hydride (60% oil dispersion). The mixture was heated at 60° C. for 20 minutes, then 2.5 ml of ethyl iodide was added. After stirring for four hours without heating, the mixture was heated to 100° C. for five minutes. Water (150 ml) was added and the mixture was cooled. The product collected was crystals of ethyl 6,7-dihydro-8-(2-ethyl-5-tetrazolyl)-5-methyl-1-oxo-1H,5H-benzo[ij]quinolizine-2-carboxylate. This product was treated with 50 ml of 1 N sodium hydroxide solution and 15 ml of methanol and heated on a steam bath for thirty minutes. The mixture was decanted into cold dilute 30% aqueous acetic acid with stirring. The product collected was white crystals of 6,7-dihydro-8-(2-ethyl-5-tetrazolyl)-5-methyl-1-oxo-1H,5H-benzo[ij]quinolizine-2-carboxylic acid which was triturated with a hexane-chloroform mixture to remove traces of mineral oil. It melted at 253° C. (dec.). Analysis: Calculated for $C_{17}H_{17}N_5O_3$: %C, 60.2; %H, 5.0; %N, 20.6; Found: %C, 60.1; %H, 5.0; %N, 20.5. The structural assignment was confirmed by infrared and nuclear magnetic resonance spectral analyses.

EXAMPLE 11

To a solution of 1.0 g (3.2 mmole) of 6,7-dihydro-5-methyl-1-oxo-8-(5-tetrazolyl)-1H,5H-benzo[ij]quinolizine-2-carboxylic acid in 30 ml of N,N-dimethylformamide was added 0.3 g sodium hydride (50% dispersion in oil). This mixture was heated at 60° C. for 30 minutes, then allowed to cool at 20° C. To this stirred mixture was added 4.0 ml (6.5 g, 35 mmole) of 1-iodo-n-butane in 5 ml of N,N-dimethylformamide. Stirring was continued for four hours. The mixture was then warmed to 80° C., and 85 ml of water was added. A solid formed which was isolated by decanting. To the solid was added 25 ml of methanol and 45 ml of 1 N sodium hydroxide solution. The mixture was heated on a steam bath for one hour, then poured into 35 ml of acetic acid and 50 ml of ice. The solid was separated by filtration, washed with 5:1 hexane/chloroform mixture and recrystallized from aqueous N,N-dimethylformamide. The product was off-white crystals of 8-(2-n-butyl-5-tetrazolyl)-6,7-dihydro-5-methyl-1-oxo-1H,5H-benzo[ij]quinolizine-2-carboxylic acid, m.p. 179° C. Analysis: Calculated for $C_{19}H_{21}N_5O_3$: %C, 62.1; %H, 5.8; %N, 19.1; Found: %C, 62.2; %H, 5.7; %N, 19.2. The structural assignment was confirmed by infrared and nuclear magnetic resonance spectral analyses.

EXAMPLE 12

Using the method of Example 11, but reacting with 2.7 g (16 mmole) of benzyl bromide in 5 ml of N,N-dimethylformamide the product obtained was 8-(2-benzyl-5-tetrazolyl)-6,7-dihydro-5-methyl-1-oxo-1H,5H-benzo[ij]quinolizine-2-carboxylic acid, m.p. 251° C. Analysis: Calculated for $C_{22}H_{19}N_5O_3$; %C, 65.8; %H, 4.8; %N, 17.5; Found: %C, 65.9; %H, 4.8; %N, 17.8. The structural assignment was confirmed by infrared and nuclear magnetic resonance spectral analyses.

EXAMPLE 13

A mixture of 0.5 g of 6,7-dihydro-5-methyl-1-oxo-8-(5-tetrazolyl)-1H,5H-benzo[ij]quinolizine-2-carboxylic acid and 50 ml of trifluoroacetic anhydride was heated at reflux for 3.5 days. Evaporation provided a residue which was diluted with water. The solid was recrystallized from aqueous N,N-dimethylformamide to provide white crystals of 6,7-dihydro-5-methyl-1-oxo-8-[2-(5-trifluoromethyl-1,3,4-oxadiazolyl)]-1H,5H-benzo[ij]quinolizine-2-carboxylic acid, m.p. 267°–268° C. Analysis: Calculated for $C_{17}H_{23}F_3N_3O_3$: %C, 53.9; %H, 3.2; %N, 11.1; Found: %C, 53.6; %H, 2.9; %N, 11.2. The structural assignment was confirmed by infrared and nuclear magnetic resonance spectral analyses.

EXAMPLE 14

A mixture of 0.5 g of 6,7-dihydro-5-methyl-1-oxo-8-(5-tetrazolyl)-1H,5H-benzo[ij]quinolizine-2-carboxylic acid and 50 ml of aceitc anhydride was heated at reflux for 24 hours. Evaporation provided a residue which was triturated with hot water. The mixture was cooled, the product separated by filtration and recrystallized from aqueous N,N-dimethylformamide to provide white crystals of 6,7-dihydro-5-methyl-8-[2-(5-methyl-1,3,4-oxadiazolyl)]-1-oxo-1H,5H-benzo[ij]quinolizine-2-carboxylic acid, m.p. 295° C. Analysis: Calculated for $C_{17}H_{15}N_3O_4$: %C, 62.8; %H, 4.6; %N, 12.9; Found:

%C 62.7; %H, 4.4; %N, 12.6. The structural assignment was confirmed by infrared spectral analyses.

EXAMPLE 15

A mixture of 1.0 g of 6,7-dihydro-5-methyl-1-oxo-8-(5-tetrazolyl)-1H,5H-benzo[ij]quinolizine-2-carboxylic acid and 5 ml (46 mmole) of phenyl isocyanate was heated at 150° C. for one hour. The mixture was then cooled and water was added. The solid was separated by filtration and recrystallized twice from aqueous N,N-dimethylformamide to provide 6,7-dihydro-5-methyl-8-[2-(5-N-anilino)-1,3,4-oxadiazolyl)]-1-oxo-1H,5H-benzo[ij]quinolizine-2-carboxylic acid solvated with N,N-dimethylformamide m.p. >300° C. Analysis: Calculated for $C_{22}H_{18}N_4O_4 \cdot C_3H_7NO$: %C, 63.1; %H, 5.3; %N, 14.7; Found: %C, 63.1; %H, 5.3; %N, 15.1.

What is claimed is:

1. A compound of the formula

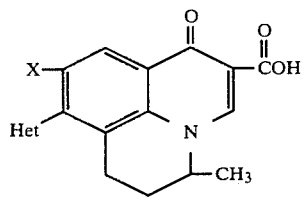

wherein Het is selected from the group consisting of 1-pyrryl, tetrazolyl of the formula

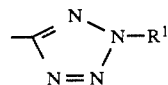

wherein $R^1$ is lower alkyl or benzyl, and oxadiazolyl of the formula

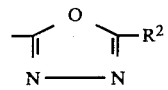

wherein $R^2$ is lower alkyl, trifluoromethyl or —NHφ; X is hydrogen, or when Het is pyrryl, X may also be fluoro; or a pharmaceutically-acceptable carboxylate salt thereof, or an alkyl or alkylaminoalkyl ester thereof having one to four carbon atoms in the alkyl group.

2. The compound 6,7-dihydro-9-fluoro-5-methyl-1-oxo-8-(1-pyrryl)-1H,5H-benzo[ij]quinolizine-2-carboxylic acid according to claim 1.

3. The compound sodium 6,7-dihydro-5-methyl-8-(2-methyl-5-tetrazolyl)-1-oxo-1H,5H-benzo[ij]quinolizine-2-carboxylate according to claim 1.

4. The compound 6,7-dihydro-8-(2-ethyl-5-tetrazolyl)-5-methyl-1-oxo-1H,5H-benzo[ij]quinolizine-2-carboxylic acid according to claim 1.

5. The compound 8-(2-benzyl-5-tetrazolyl)-6,7-dihydro-5-methyl-1-oxo-1H,5H-benzo[ij]quinolizine-2-carboxylic acid according to claim 1.

6. The compound 6,7-dihydro-5-methyl-1-oxo-8-[2-(5-trifluoromethyl-1,3,4-oxadiazolyl)]-1H,5H-benzo[ij]quinolizine-2-carboxylic acid according to claim 1.

7. The compound 6,7-dihydro-5-methyl-8-[2-(5-methyl-1,3,4-oxadiazolyl)]-1-oxo-1H,5H-benzo[ij]quinolizine-2-carboxylic acid according to claim 1.

8. The compound 6,7-dihydro-5-methyl-8-[2-(5-N-anilino)-1,3,4-oxadiazolyl)]-1-oxo-1H,5H-benzo[ij]quinolizine-2-carboxylic acid according to claim 1.

9. The compound 6,7-dihydro-5-methyl-1-oxo-8-(1-pyrryl)-1H,5H-benzo[ij]quinolizine-2-carboxylic acid according to claim 1.

10. A composition for inhibiting the growth of microorganisms comprising an effective amount of the compound according to claim 1 formulated in a pharmaceutically-acceptable vehicle.

11. A method of inhibiting the growth of microorganisms comprising contacting said microorganisms with an effective amount of a compound according to claim 1.

* * * * *